US007651543B1

(12) United States Patent
Marple et al.

(10) Patent No.: US 7,651,543 B1
(45) Date of Patent: Jan. 26, 2010

(54) OMNI-DIRECTIONAL INLET FOR PARTICULATE COLLECTION

(75) Inventors: Virgil A. Marple, Maple Plain, MN (US); Bernard A. Olson, Arden Hills, MN (US); Alan W. Hall, King George, VA (US); Edward A. Lustig, Jr., Charlotte Hill, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 723 days.

(21) Appl. No.: 11/482,295

(22) Filed: Jun. 26, 2006

(51) Int. Cl.
*B01D 50/00* (2006.01)

(52) U.S. Cl. .............................. 55/320; 55/315; 55/318; 73/863.23; 73/28.04; 73/28.05; 73/863.21; 73/863.22; 73/28.01; 96/413

(58) Field of Classification Search ............... 55/320, 55/318, 315; 73/28.05, 28.04, 28.01, 863.21–863.23; 96/413

See application file for complete search history.

(56) References Cited

U.S. PATENT DOCUMENTS

| | | | | |
|---|---|---|---|---|
| 2,780,826 A | * | 2/1957 | Montgomery et al. | 15/327.3 |
| 3,578,758 A | * | 5/1971 | Altshuler | 73/40.7 |
| 4,038,057 A | * | 7/1977 | Roth | 73/863.22 |
| 4,067,705 A | * | 1/1978 | Kurz | 73/863.03 |
| 4,151,742 A | * | 5/1979 | Howlett | 73/28.04 |
| 4,235,098 A | * | 11/1980 | Tisch | 73/863.23 |

(Continued)

OTHER PUBLICATIONS

V. A. Marple et al., "Inertial, Gravitational, Centrifugal, and Thermal Collection Techniques", *Aerosol Measurement: Principles, Techniques and Applications*, 2/e, P. A. Baron et al., eds, Wiley-Interscience ©2001, Chap. 10, pp. 229-260.

(Continued)

*Primary Examiner*—Jason M Greene
*Assistant Examiner*—Anthony Shumate
(74) *Attorney, Agent, or Firm*—Gerhard W. Thielman, Esq.

(57) ABSTRACT

A planar omni-directional inlet assembly is provided for installing on a device, such as a dry filter unit, that draws a fluid medium, such as ambient air, to collect particulate matter suspended in the fluid medium onto a filter. The inlet assembly includes an annular platform removably positionable on the device; an annular nozzle to direct the air from the platform; an annular impactor disposed downstream of the nozzle; a housing that disposes the filter downstream of the impactor; and an exit for passing the air from the filter to the device. The impactor presents a flow obstacle for a portion of the particulate matter. The housing directs the air through the filter. The housing includes a base with a first cavity and a lid with a second cavity such that the filter is disposable between the first and second cavities.

19 Claims, 4 Drawing Sheets

U.S. PATENT DOCUMENTS

| | | | | |
|---|---|---|---|---|
| 4,382,808 | A | * | 5/1983 | Van Wormer et al. .......... 55/418 |
| 4,461,183 | A | * | 7/1984 | Wedding .................. 73/863.21 |
| 4,649,760 | A | * | 3/1987 | Wedding .................. 73/863.23 |
| 4,796,475 | A | * | 1/1989 | Marple .................... 73/863.22 |
| 5,040,424 | A | | 8/1991 | Marple et al. ............. 73/863.23 |
| 5,160,513 | A | | 11/1992 | Koves ............................ 55/76 |
| 5,412,975 | A | | 5/1995 | Raabe et al. ................ 73/28.04 |
| 6,077,485 | A | * | 6/2000 | Baker .......................... 422/300 |
| 6,251,152 | B1 | | 6/2001 | Thiele .......................... 55/318 |
| 7,082,811 | B2 | | 8/2006 | Marple et al. .............. 73/28.05 |
| 7,305,895 | B1 | | 12/2007 | Andrews et al. ......... 73/863.41 |
| 7,334,453 | B2 | * | 2/2008 | Trakumas et al. .......... 73/28.05 |
| 2002/0129538 | A1 | * | 9/2002 | Buzzell ......................... 43/55 |

OTHER PUBLICATIONS

B. Y. H. Liu et al., "Aerosol Sampling Inlets and Inhalable Particles", *Atmospheric Environments*, Elsevier ©1981, v. 15, pp. 589-600.

Sholkovitz, E. et al., "An autonomous aerosol sampler/elemental analyzer designed for ocean buoys and remote land sites", *Atmospheric Environment*, Elsevier ©2001, v. 35 pp. 2069-2975.

EMEP/CCC-Note1/2000 "Measurement of Aerosol Particle Mass and Chemical Speciation of Aerosol Particles".

\* cited by examiner

OMNI-DIRECTIONAL INLET FOR PARTICULATE COLLECTION

STATEMENT OF GOVERNMENT INTEREST

The invention described herein was made in the performance of official duties by one or more employees of the Department of the Navy and/or under Contract Order N00178-05-M-3100, and thus, the invention herein may be manufactured, used or licensed by or for the Government of the United States of America for governmental purposes without the payment of any royalties thereon or therefor.

BACKGROUND

The invention relates generally to the sampling of moving fluids such as moving airflows, and more particularly to a sampling system that extracts samples of a moving fluid passing thereover. The moving fluid as a medium may represent a variety of gases. Matter to be sampled may represent solid particles or liquid droplets or other material physically or chemically distinguishable from the suspension medium.

As an example, airflows may be sampled in support of a variety of flow monitoring applications for determining aerosol content, or conforming microbiological presence, using standard microbiological techniques. The Dry Filter Unit (DFU) 1000 represents an exemplary air sampling device for collecting, for example, bio-particulates from suspension in ambient air for analysis. The DFU-1000 provides a pressure differential to draw air within, thereby enabling particles to be collected. Note that "ambient air" corresponds in this document to nominal temperature of 20° C. (degrees Celsius) and pressure of 101 kPa (kilopascals).

Figure 1A:
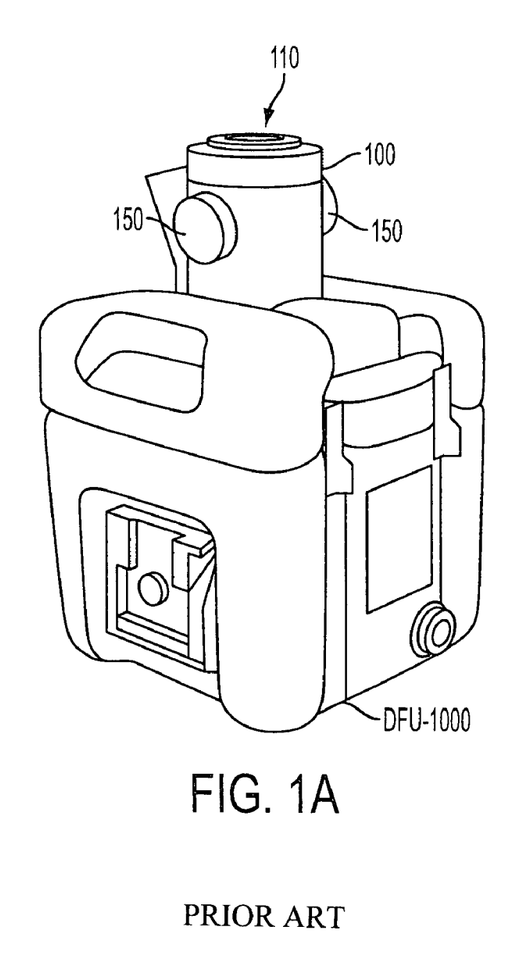
FIG. 1A is an isometric view of a Dry Filter Unit (DFU-1000) equipped with a conventional inlet assembly.

Particles smaller than a specific size may be categorized under an Environmental Protection Agency standard as specified under Title 40 of the Code of Federal Regulations (CFR). For example, particle measurement PM-10 under 40 CFR §50.6(c) corresponds to particles having effective diameters no larger than 10 μm (microns). Similarly, PM2.5 under 40 CFR §50.7(a)(1) corresponds to particles no larger than 2.5 μm. FIG. 1A shows an exemplary isometric view of the DFU-1000.

The DFU-1000 houses a pump/blower and is configured in a one-person portable carrying case for 40,000 hour-life continuous duty. The DFU-1000 may use commercially available power at 120/240 $V_{AC}$ (volts) from alternating current at 50/60 Hz (hertz) or else direct current sources adaptable using an optional auxiliary power pack of 24 $V_{DC}$. The DFU-1000 has dimensions of 15 in (inches) high, 13 in wide and deep, a mass of 42 $lb_m$ (pounds-mass). The power requirements are 5.6 A (amps) at operation and 17 A starting at 120 $V_{AC}$.

Figure 1B:
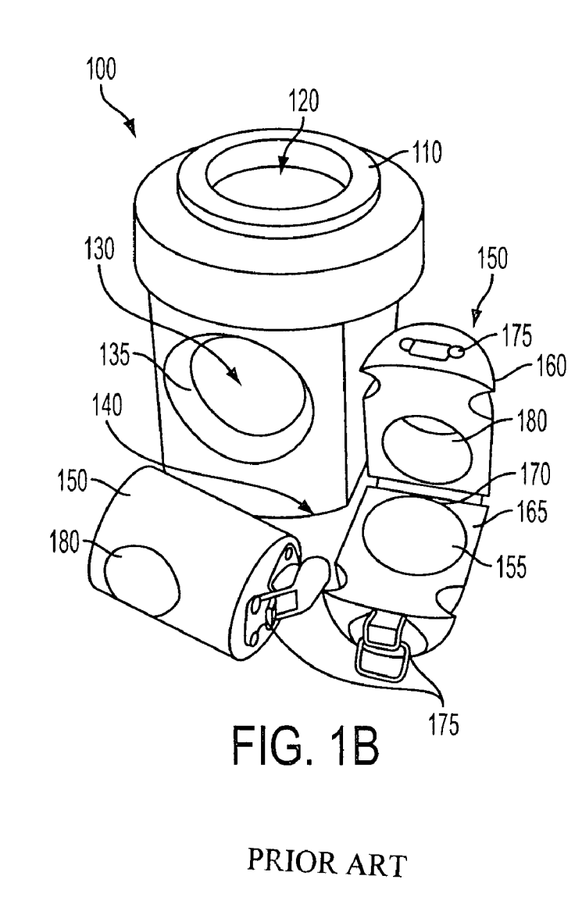
FIG. 1B is an isometric exploded-diagram view of the conventional inlet assembly.

The DFU-1000 may be conventionally equipped with an open-top tandem-chamber inlet assembly 100 shown in FIG. 1B in isometric view as an exploded diagram. Air flows over a top-facing orifice 110 into which particulate matter descends entrained in an air stream at low velocity to an entrance chamber 120. The air stream passes from the entrance chamber 120 through a forked pair of twin filter chambers 130 and rejoins in an exit chamber 140 to enter a top port of the DFU-1000, which draws in the air.

Each of the twin chambers 130 houses a cylindrical filter holder 150 that secures a polyester mesh filter 155 having a diameter of approximately 1.5 in. Each chamber 130 incorporates a foam seal 135 to avoid pressure drop losses between the inlet 110 and the exit 140. The filter 155 traps particles larger than those that pass through its mesh. The resulting collection from the filter 155 may include particles of interest for further analysis as well as others larger than desired but collaterally entrapped nonetheless.

The holder 150 may comprise two halves 160, 165 pivotably connected to a molded hinge 170 and securable together when closed by a latch 175. The holder 150 may be opened by disconnecting the latch 175 to remove and replace the filter 155. Contents collected on the removed filter may then be analyzed at a separate facility. When the holder 150 is open, the filter 155 may be inserted into recesses 180, one of which being equipped with baffles that prevent the filter 155 from being dislodged by the pressure differential produced by the DFU-1000.

Artisans of ordinary skill will recognize that the air intake described for the DFU-1000 represents an example application, and will recognize that other devices for drawing or otherwise moving fluid medium to enable particulate matter collection may be contemplated, accordingly.

SUMMARY

Practical limitations of the conventional inlet assembly include, but not limited to, reduced effectiveness in capturing particles within the target range with increasing wind speed (from interference with the pressure differential due to aspiration), as well as equipment degradation from operational handling, precipitation or other environmental conditions, such as dust or sea-spray. Moreover, the conventional inlet cannot inherently filter out particles larger than those of interest (e.g., dust). Such larger particles deposit onto the filter, which complicate subsequent analysis of the particulate matter. For example, biological sampling may produce erroneous results from introduction of organisms (e.g., small insects).

Various exemplary embodiments provide a planar omni-directional inlet assembly (within a horizontal airflow plane) a planar omni-directional inlet assembly for installing on a device that draws a fluid medium to collect particulate matter suspended in the fluid medium onto a filter. In particular, the inlet assembly includes a platform forming an annular inlet to receive the fluid medium positionable on the device; an annular nozzle to direct the fluid medium from the platform; an annular impactor disposed downstream of the annular nozzle; a housing that disposes the filter downstream of the impactor; and an exit for passing the fluid medium from the filter to the device, the exit being disposed downstream of the housing. The impactor presents a flow obstacle for a portion of the particulate matter. The housing directs the fluid medium through the filter and is removably disposable on the platform.

In a preferred embodiment, the inlet assembly operates wherein the fluid medium is ambient air and the device is a dry filter unit (DFU). Additional embodiments provide the housing as a filter holder for securing a particulate filter in an inlet assembly for installing on a DFU that draws in ambient air to collect its entrained particulate matter on the filter. In particular, the filter holder includes a base; a lid; and a hinge. The base has a first cavity that communicates with the DFU and is removably disposable on the inlet assembly along a sealable surface of the base. The lid has a second cavity that communicates with the inlet assembly and is disposable against the base opposite the sealable surface in a closed position. The filter is disposable between the first and second cavities. The hinge pivotably connects the base and the lid to enable an edge of the lid opposite the hinge to swing away from the base in an open position.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

Service personnel periodically remove the filters in an inlet assembly to analyze the collected contents trapped thereon. Concurrently, the filters are replaced to ensure continued proper operation of the associated dry filter unit. Such duties may be performed under minimal illumination and/or while clad in cumbersome environmental protection gear. These conditions can inhibit expeditious filter replacement due to consequent sensory and/or manipulatory degradation. Various exemplary embodiments replace the conventional inlet assembly with a retrofitted planar omni-directional inlet to improve particle collection performance, enhance maintenance and minimize alteration to existing systems. Such systems may include any appropriate device suitable for drawing a fluid medium therethrough to enable collection of particles entrained therein. The DFU-1000 represents but a single example of such a device.

Figure 2:
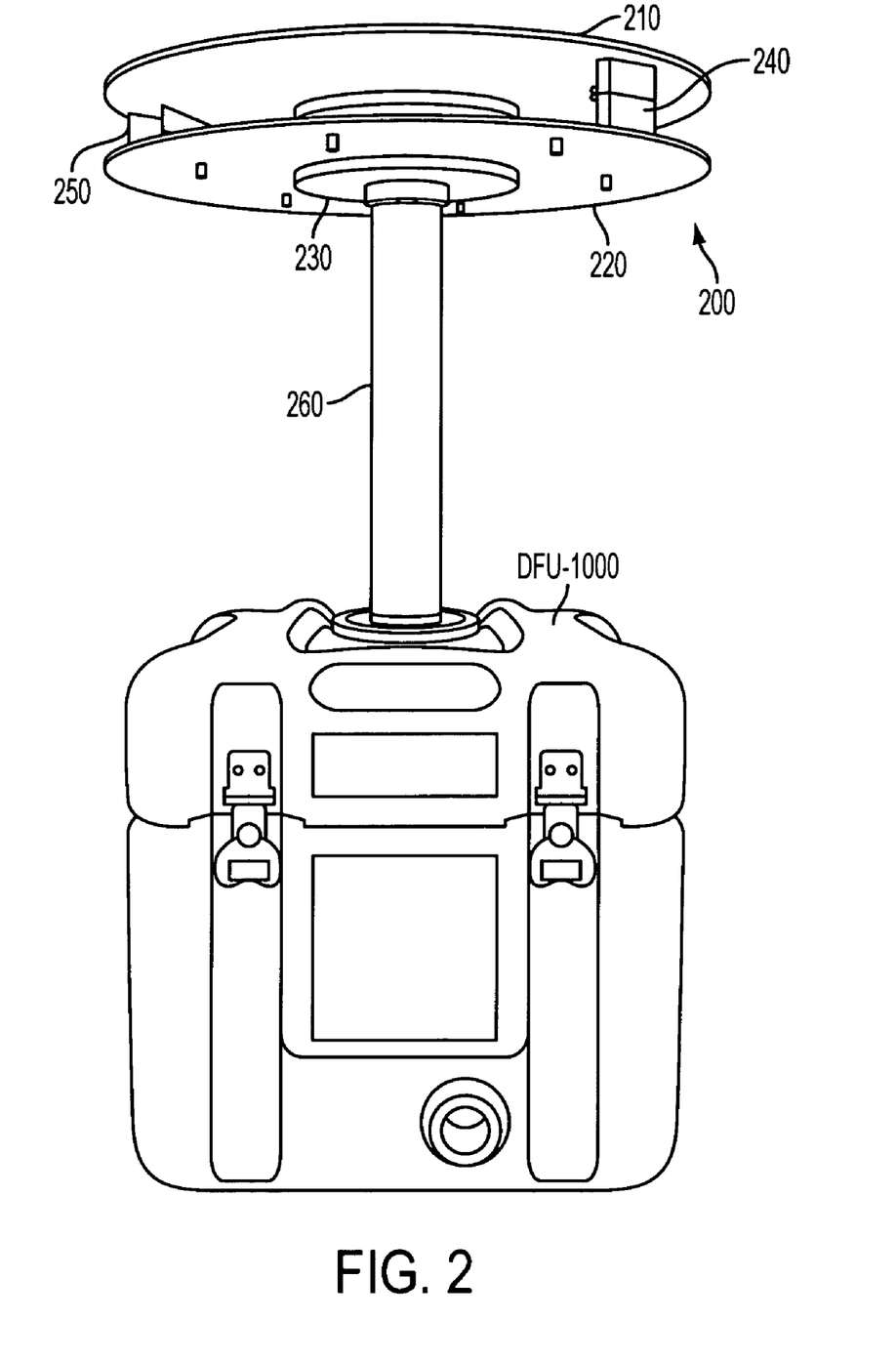
FIG. 2 is an isometric view of the DFU-1000 with a planar omni-directional inlet.

FIG. 2 shows an exemplary embodiment of an inlet unit 200 for the DFU-1000. In the configuration described herein, the inlet unit 200 may include opposing upper and lower circular plates 210, 220. In FIG. 2, the plates 210, 220 are disposed parallel to each other in a closed position for operation with the DFU-1000. The plates 210, 220 facing each other may preferably be flat and circular in plan-form (i.e., from top view), although other shapes may be used without departing from the spirit of the invention. A mounting flange 230 may be attached to the lower plate 220. The plates 210, 220 may be connected to each other by a pair of inlet hinges 240 and an inlet latch 250. The flange 230 may connect to a tube 260 leading to the top port of the DFU-1000.

Figure 3A:
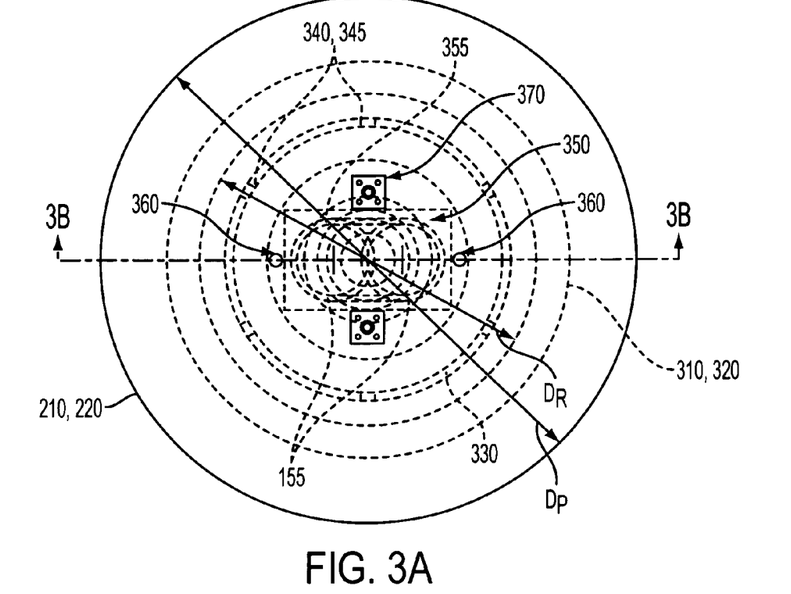
FIGS. 3A and 3B are plan and elevation diagrams of the planar omni-directional inlet assembly.
Figure 3B:
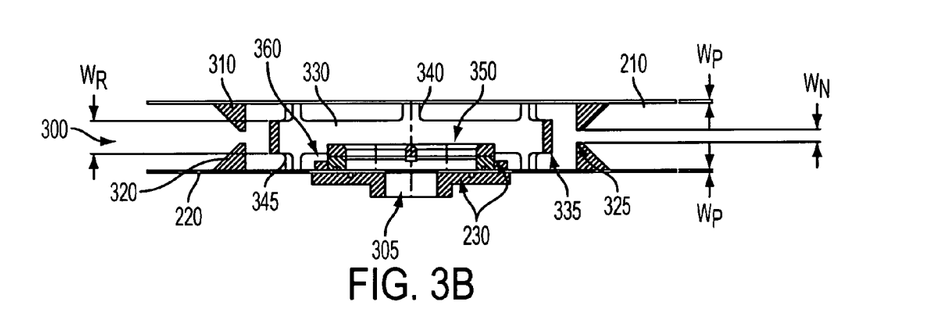

FIG. 3A illustrates the exemplary embodiment of the inlet unit 200 as a plan (top) view from above. Similarly, FIG. 3B provides a complimentary elevation (side) view of the inlet unit 200 along section A-A. The plates 210, 220 may be dimensionally characterized by a plate diameter $D_P$ and a plate thickness $W_P$. An annulus or annular nozzle 300, axisymmetric about an axis 305, includes upper and lower portions 310, 320. The annular opening 325 formed by the nozzle 300 may be characterized by a nozzle throat width $W_N$ for the separation distance between the portions 310, 320.

Air passing along the inlet unit 200 may flow along the plates 210, 220 and directed along the sloping ramps of the portions 310, 320 through the nozzle opening 325. The upper and lower portions 310, 320 may be secured to their corresponding upper and lower plates 210, 220 by threaded screws or bolts, for example. An annular concentric impact ring 330 may be disposed inward and downstream of the nozzle 300 relative to an oncoming flow of the passing air.

The impact ring 330 may present a flat cross-section 335 as shown in FIG. 3B. Alternatively, the cross-section may alternatively present concave or convex surfaces to the oncoming flow. The impact ring 330 presents an obstacle to particles (particulate matter) suspended in the passing air. Depending on the flow velocity through the nozzle 300 and the characteristic dimensions of the inlet unit 200, large particles are more likely to strike the impact ring 330 than small particles as a consequence of differences in inertia and drag behavior.

Particles that avoid striking the impact ring 330 may impact upon the interior surfaces of one of the plates 210, 220 as the flow bends around the impaction plate 330 and flows between the supports 340 and 345. The plates 210, 220 represent secondary impaction surfaces that may further restrict particles to those within a targeted size range to be collected on the filter 155.

The impact ring 330 may be positioned relative to the plates 210, 220 by angularly distributed upper and lower legs 340, 345. The cylindrical dimensions of the impact ring 330 may be characterized by a ring width $W_R$ and a ring diameter $D_R$, respectively. In particular, the drawings feature six complimentary pairs of legs 340, 345 distributed 60° apart, although other angular arrangements may be contemplated without departing from the inventive features disclosed herein.

The upper legs 340 provide separation distance between the impact ring 330 and the upper plate 210. Similarly, the lower legs 345 provide separation distance between the impact ring 330 and the lower plate 220. One of these sets of legs 340, 345 may be secured to their corresponding plates 210, 220 by bolts.

One or more filters 155 may be replacably contained within a removable filter housing 350. The housing 350 may be removably disposed on the lower plate 220 above the flange 230. To reduce flow leakage from the lower plate 220, the housing 350 may include an O-ring in an annular groove 355 on its bottom surface and around the region containing the filters 155. The housing 350 may be positioned between an opposing pair of alignment bolts 360 and detachably secured by an opposing pair of clamping block 370.

Figure 4A:
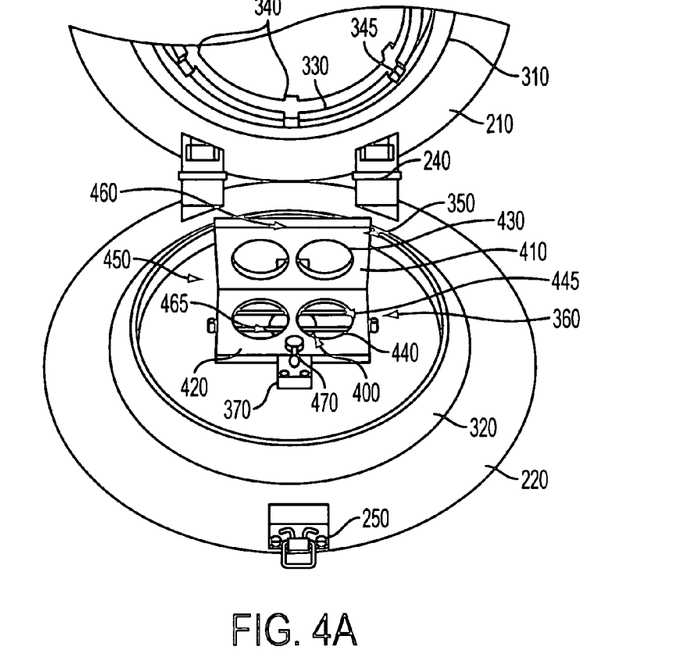
FIGS. 4A and 4B are isometric detail views of the planar omni-directional inlet assembly.
Figure 4B:
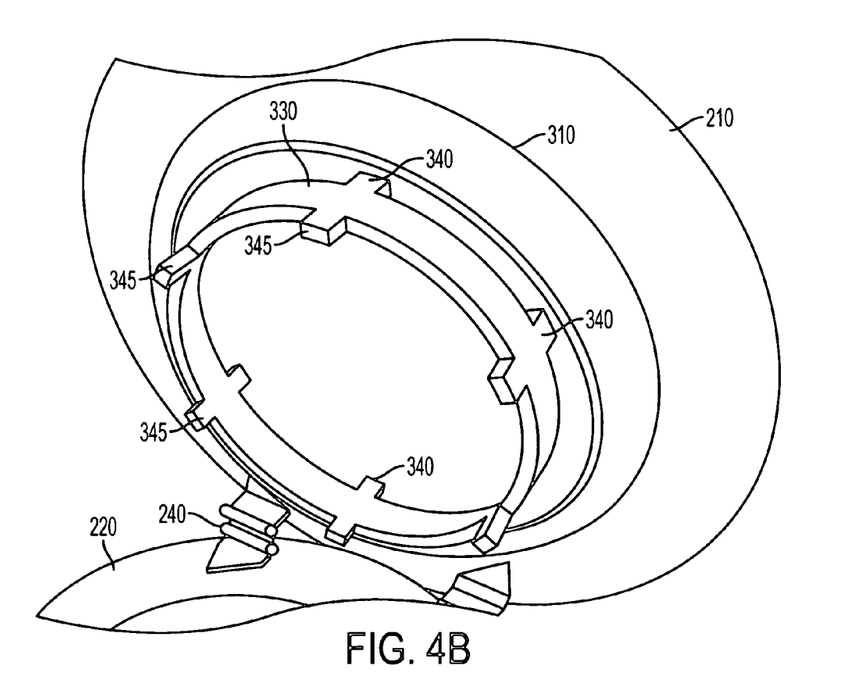

FIGS. 4A and 4B illustrate isometric views of the inlet unit 200 with the upper and lower plates 210, 220 unlatched and open to enable filter replacement. In particular, the inlet latch 250 is released and the upper plate 210 swings on the inlet hinges 240 substantially perpendicular to facilitate access to the housing 350. As shown, the impact ring 330 may be secured to the upper plate 210 at the upper legs 340, while the lower legs 345 may operationally separate from engagement with the lower plate 220.

The housing 350, disposed over the lower plate 220 over an orifice 400 in the flange 230, represents a hinged rectangular container for a pair of filters 155. The housing 350 includes a lid 410 and a base 420. The lid 410 exhibits a pair of receiver openings 430, complimented by corresponding egress openings 440 in the base 420. One of these sets of openings 430, 440 may feature baffles 445 or containment grids, to secure the filter 155 from becoming entrained in the flow, as well as provide a tactile orientation reference for an operator that services under conditions of low illumination. In the configuration shown in FIG. 4A, the baffles 445 are featured in conjunction with the egress openings 440.

The lid 410 and the base 420 may be connected together by hinges 450, shown as a tandem pair at corners of opposite sides, and by an opposing pair of permanent magnets 460, 465 recessed respectively within the lid 410 and the base 420 so as oppose or face each other. The hinges 450 may form a pivot axis substantially parallel to the lower plate 210. The first magnet 460 is disposed on an inner surface of the lid 410 to present a first magnetized surface. The second magnet 465 is disposed on an inner surface of the base 420 to present a second magnetized surface.

The surfaces of the first and second magnets 460, 465 have opposite polarity so as to attract each other and secure the housing 350 to the closed position when shut. The strength of the magnetic field by the magnets 460, 465 may be gauged to an appropriate level to prevent the housing 350 from accidentally opening, but to enable an individual to resist the magnetic attraction by unaided hands. Use of magnets reduces the possibility of operator clothing and/or skin getting caught or torn while handling the holder and/or changing filters. Developing a small rip in protective gear may cause hazardous exposure, and manipulating small latches and hooks while wearing cumbersome protective gear can be cumbersome.

As will be apparent to skilled artisans, alternate configurations may be contemplated using two or more opposing pairs of magnets and/or positions along pivoting faces of the lid 410 and the base 420 (rather than along the sides) without departing from the spirit of the invention. Additionally, alternate configurations may be contemplated that employ alternate mechanisms to align and secure the lid 410 and the base 420 to each other, such as latches, hooks, threaded bolts and/or combinations thereof.

The housing 350 may be removable from the lower plate 220, rather than be permanently fastened. Instead, the alignment bolts 360 enable an operator to position the housing 350 therebetween to cover the orifice 400. Each clamping block 370 releasably secures the housing 350 by pivoting clamps 470. The clamp 470 lifts away from its corresponding block 370 when releasing the housing 350, and lowers onto the lid 410 when securing the housing 350 to the lower plate 220. The clamp 470 may pivot along a hinge substantially parallel to the lower plate 210 so that a lever engages the housing 350 when lowered and releases the housing 350 when lifted. The bolts 360 and the block 370 may be discernable by tactile sensation. Skilled artisans will recognize that alternate configurations of alignment indicators are possible without departing from the scope of the invention.

The plates 210, 220, nozzle 300 and the housing 350, as fabricated by Applicants, are preferably composed substantially of anodized Al-6061 aluminum alloy suitable for harsh weather conditions, convenient portability and stringent reliability of service requirements. Further, Applicants provide simplicity in the above-described embodiments by eliminating items vulnerable to corrosion, such as screws and moving parts, and by configuring all surfaces to be readily reachable for cleaning. However, skilled artisans will recognize that the design principles disclosed herein are also applicable to alternate materials for different circumstances for applications for either milder conditions or shorter longevity requirements, such as more economically produced designs that use plastic, sheet steel or other suitable material produced by molding or casting.

Additionally, the exemplary dimensions described may most preferably include plate diameter $D_P$=16 in (inches), ring diameter $D_R$=10 in, nozzle width $W_N$=0.313 in, ring width $W_R$=1.000 in, plate thickness $W_P$=0.090 in. However, skilled artisans will recognize that the design principles disclosed herein are also applicable to alternate geometries and dimensional constraints.

Figure 5:
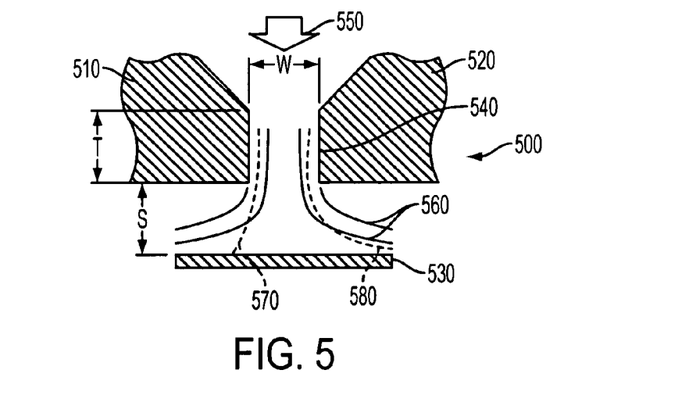
FIG. 5 is an elevation view diagram of particle impaction in conjunction with an inlet flowstream.

FIG. 5 is an elevation view diagram adapted from Marple, V. A.; Olson, B. A.; Rubow, K. L., "Inertial, Gravitational, Centrifugal, and Thermal Collection Techniques", chap. 10 of *Aerosol Measurement: Principles, Techniques, and Applications*, $2^{nd}$ Edition, Baron, P. A.; Willeke, K. eds., Wiley, ©2001, incorporated herein by reference. An inlet 500 is comprised from left and right portions 510, 520 of an acceleration nozzle and an impaction plate 530. The nozzle converges to a throat 540 having a gap width W and a thickness T. The impaction plate 530 is separated from the nozzle by a distance S. The geometry is important for the proper operation of the device by controlling the flow and aerosol impaction phenomena.

An air flow 550 approaches the nozzle and passes through the throat 540 towards the impaction plate 530 along streamlines 560. Under subsonic adiabatic conditions, the air flow 550 accelerates as the path width decreases. Aerosol particles entrained in the air flow 550 possess drag characteristics that may differ from the ambient air.

A first particle with abundant inertia may impact the impaction plate 530 at the end of a first trajectory 570. A second particle with much less inertia, such as one smaller than the first particle, may evade the impaction plate 530 along a second trajectory 580. Because bio-agent particles to be analyzed are typically smaller than dust and sand commonly suspended in ambient air, the impaction plate 530 may bar the dust and sand so that filters 155 within a unit 200 trap the bio-agents as a larger fraction of the particulate matter collected.

The following example provides quantified values to demonstrate the impaction effects. Stokes number, St, represents a non-dimensional parameter to characterize aerodynamic properties (e.g., inertia) of the particles, with values approximately exceeding unity serving to predict particle impaction. Stokes number may be expressed from Marple as $St=\rho_p C_c d_p^2 U/(9\eta W)$, where $\rho_p$ is the particle density, $C_c$ is the Cunningham slip correction factor, $d_p$ is the effective particle diameter, U is the medium flow velocity, $\eta$ is the medium dynamic viscosity and W is the nozzle gap width. Much of the technical literature labels viscosity by the symbol $\mu$, but to reduce confusion from its incorporation for micro-units, $\eta$ is used herein.

The slip correction factor $C_c$ is an empirically derived parameter based on a dimensionless Knudsen number, Kn, that relates the gas molecular mean free path $\lambda$ to the particle diameter by $Kn=2\lambda/d_p$. For large particles in continuum flow (e.g., ambient air $\lambda$=0.0665 μm), Kn<<1. In contrast, for Kn≈1, particles may slip past the obstacles of air molecules.

Slip correction may be calculated based on particle elasticity characteristics and the medium physical properties. For solid particles, the slip correction factor may be approximated as $C_c \approx 1+1.142$ Kn. Reynolds number, Re, represents a dimensionless ratio between inertial and kinetic (or frictional) forces, as expressed by nozzle jet $Re_j=\rho UW/\eta$, where $\rho$ is the medium density. Boundary-constrained flow regimes may be classified as laminar for Reynolds number below the transition value of ~4000, or above for nozzle convergence.

For crystalline silica particulates from ground quartz as an example, the following quantities may be used: particle density $\rho_p$=2660 kg/m³ (kilograms-per-cubic-meter) and $d_p$=2.8 μm. The corresponding slip correction factor may be approximated as $C_c \approx 1.054$. Based on the above-described geometry of the nozzle 300, the throat width W=0.00795 m (meter). For the medium as ambient air, $\rho$=1.205 kg/m³, $\eta$=18.203×10$^{-6}$ Pa-s (pascal-second). Velocity through the nozzle may be estimated at 2 m/s (meters-per-second). From these values, St≈0.033, $Re_j$=1050 and Kn≈0.05. These values predict that these fine quartz crystals would easily pass through the inlet 200 (St<<1) in laminar continuum flow ($Re_j$<4000, Kn<<1).

The distribution of particles according to size for high-bypass (i.e., small particle diameter) selection may be tailored by adjusting the flow characteristics of the air into the inlet unit 200. Parameters to adjust may include flow rate and inlet geometry. Specifically, particles suspended in the air that pass through the nozzle 300 may be divided into three groups: (a) large particles that are substantially all collected on the impact ring 330; (b) small particles that are substantially detoured by the impact ring 330 towards the housing 350; and (c) intermediate particles of which a portion impinge and another portion deflect around the impact ring 330. Minimization of the intermediate group may define the quality of a "cut" that segregates the high bypass particles intended for filter collection and subsequent analysis.

The "cut" may be refined by staging a series of concentric impact rings that may be augmented by associated intermediate annular nozzles disposed between the rings. This improves the "cut" by reducing the intermediate group of particles, but may yield loss of desired particles due to possible unintended impaction on additional surface area. Alternatively, the series may cascade slightly different rings and nozzles, each with a slightly smaller "cut", as shown in Marple. By concatenating the interception of the particles, the fraction of intermediate particles may be reduced and the distribution of particle sizes that reach the filter housing 350 disposed in the center of the ring series may be tightened. In a similar fashion, to additionally exclude particles below a specified size, the housing 350 may be disposed at a position between selected concentric rings for high-and-low bypassing of particles that reach the filter 155 by impact as the remaining particles continue to the unit exit at the flange 230.

The exemplary embodiments of the inlet unit 200 described herein provide several advantages to analysts assigned to evaluate the particles received from the filter 155, thereby improving efficiency of the analysis by increasing the quantity of desired particle sizes within a given air flow. (Artisans of ordinary skill should note that the inlet unit 200 as described is designed to have a higher collection efficiency to thereby grab more particles out of the air than the conventional inlet, rather than act as a concentrator.)

Some of these advantages include: (a) a planar omni-directional inlet configuration using parallel plates 210, 220 with an omni-directional axisymmetric nozzle that allows wind-blown air to flow into the inlet unit 200 from any horizontal direction as well as avoid precipitation; (b) an impact ring 330 to selectively restrict particles by size for entry into the filter 155 to thereby reduce analysis error from large particle debris; (c) an O-ring seal within a groove 355 between the housing 350 and the lower plate 220 to reduce pressure drop degradation within the inlet unit 200. In particular, the nozzle-impactor combination serve to route aerosol particles within a target size range more effectively to the filters, in addition to having greater resistance to intrusion of large objects, such as insects. Also, the improved seal improves flow stability, and inhibits particles of interest from leaking through an alternate exit.

The exemplary embodiments of the inlet unit 200 described herein provide several advantages to field operators assigned to replace filters 155 over conventional arrangements. These advantages are intended to facilitate and simplify manipulation while the operators wear cumbersome gear, lack a sophisticated suite of tools and perform duties under low illumination. Some of these advantages include: (a) absence of toggles to open; (b) magnetic fasteners 460, 465 to close the housing; tactile indicators to orient and align the housing 350 for disposing onto the lower plate 220; (c) schedule reduction in filter replacement frequency due to reduced non-target particulate matter from being collected on the filter 155 (i.e., improved selectivity of particles), as well as reduced filter degradation from precipitation; (d) no loose or moving parts; and (e) a replaceable filter housing 350 that can be loaded and unloaded in a laboratory environment separate from the inlet unit 200.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A planar omni-directional inlet assembly for installing on a device that draws a fluid medium to collect particulate matter suspended in the fluid medium onto a filter, the inlet assembly comprising:

a platform forming an annular inlet to receive the fluid medium, the platform being disposable on the device and including opposing plates disposable to be parallel to each other, an annular nozzle to direct the fluid medium from the platform and the annular nozzle comprises a pair of nozzle portions, each of the pair of nozzle portions is respectively disposed on a corresponding member of the opposing plates;

an annular impactor disposed downstream of the annular nozzle, the impactor presenting a flow obstacle for a portion of the particulate matter;

a housing that disposes the filter downstream of the impactor, the housing directing the fluid medium through the filter, the housing being removably disposable on the platform; and an exit for passing the fluid medium from the filter to the device, the exit being disposed downstream of the housing.

2. The inlet assembly according to claim 1, wherein the platform comprises opposing plates disposable to be substantially parallel to each other.

3. The inlet assembly according to claim 2, wherein the platform further comprises a plate hinge to pivotably connect the opposing plates to be closed while substantially parallel in an operating configuration and open while at least one plate of the opposing plates swings on the hinge away from the other plate.

4. The inlet assembly according to claim 2, wherein the platform further comprises a plate latch to releasably attach the opposing plates.

5. The inlet assembly according to claim 1, wherein the platform includes at least one indicator for aligning the housing for disposal on the platform, the indicator being discernable by at least tactile sensation.

6. The inlet assembly according to claim 1, wherein the platform includes a clamp to releasably attach the housing to the platform.

7. The inlet assembly according to claim 1, wherein the annular nozzle comprises a pair of nozzle portions disposable to be parallel to each other on the platform.

8. The inlet assembly according to claim 1, wherein the housing comprises hinged members positionable to open and closed positions.

9. The inlet assembly according to claim 8, wherein the hinged members comprise a complimentary pair of members that oppose each other, each member including a recess that contains a magnet therein, such that the magnet exposes a magnetized surface, the magnets being disposed opposite each other while the hinged members are in the closed position, the magnetized surfaces having opposite polarity to each other.

10. The planar omni-directional inlet assembly in accordance with claim 1 wherein the fluid medium is air and the device is a dry filter unit (DFU).

11. A filter holder for securing a particulate filter in the inlet assembly according to claim 1 for installing on a device that draws a fluid medium to collect particulate matter suspended in the fluid medium onto a filter, the filter holder comprising:
- a base having a first cavity that communicates with the device, the base being removably disposable on the inlet assembly along a sealable surface of the base;
- a lid having a second cavity that communicates with the inlet assembly, the lid being disposable against the base opposite the sealable surface in a closed position; and
- a hinge that pivotably connects the base and the lid to enable an edge of the lid opposite the hinge to swing away from the base in an open position, wherein the filter is disposable between the first and second cavities.

12. The filter holder according to claim 11, wherein the base further includes an annular groove for receiving an O-ring to seal an interface between the base and the inlet assembly.

13. The filter holder according to claim 11, wherein the base and the lid each further includes a recess that contains a magnet therein, such that the magnet exposes a magnetized surface, the magnets being disposed opposite each other while the base and the lid are in the closed position, the magnetized surfaces having opposite polarity to each other.

14. A planar omni-directional inlet assembly for installing on a device that draws a fluid medium to collect particulate matter suspended in the fluid medium onto a filter, the inlet assembly comprising:
- a platform forming an annular inlet to receive the fluid medium, the platform being disposable on the device and including opposing plates disposable to be parallel to each other,
- an annular nozzle to direct the fluid medium from the platform and the annular nozzle comprises a pair of nozzle portions each of the pair of nozzle portions is respectively disposed on a corresponding member of the opposing plates;
- a plurality of annular impactors disposed downstream of the annular nozzle;
- a housing that disposes the filter downstream of at least one of the annular impactors, the housing directing the fluid medium through the filter, the housing being removably disposable on the platform; and
- an exit for passing the fluid medium from the filter to the device, the exit being disposed downstream of the housing.

15. The inlet assembly according to claim 14, wherein the annular impactors include outer and inner impactors, the outer impactor being disposed downstream of the annular nozzle, the inner impactor being disposed downstream of the outer impactor.

16. The inlet assembly according to claim 15, wherein the housing is disposed downstream of the outer impactor and upstream of the inner impactor.

17. The inlet assembly according to claim 14, wherein the platform includes at least one indicator for aligning the housing for disposal on the platform, the indicator being discernable by at least tactile sensation.

18. The inlet assembly according to claim 14, wherein the platform includes a clamp to releasably attach the housing to the platform.

19. The inlet assembly according to claim 1, wherein each portion of the pair of nozzle portions opposes the other in tandem symmetrically to a plane perpendicular to an axis of symmetry of the opposing plates.

* * * * *